United States Patent [19]

Leininger et al.

[11] 4,137,922
[45] * Feb. 6, 1979

[54] DILATOR FOR CERVICAL CANAL

[75] Inventors: Robert I. Leininger; Joseph R. Preston; Brenton R. Lower, all of Columbus, Ohio

[73] Assignee: Ortho Pharmaceutical Corp., Raritan, N.J.

[*] Notice: The portion of the term of this patent subsequent to Aug. 19, 1992, has been disclaimed.

[21] Appl. No.: 579,631

[22] Filed: May 21, 1975

Related U.S. Application Data

[63] Continuation-in-part of Ser. No. 338,697, Mar. 7, 1973, Pat. No. 3,900,033.

[51] Int. Cl.$^2$ ............................................. A61M 29/02
[52] U.S. Cl. ................................................... 128/344
[58] Field of Search ......................... 128/242, 246, 344

[56] References Cited

U.S. PATENT DOCUMENTS

| 1,735,519 | 11/1929 | Vance | 128/344 |
| 2,499,045 | 2/1950 | Walker et al. | 128/344 X |
| 3,046,988 | 7/1962 | Moreau et al. | 128/344 X |
| 3,480,017 | 11/1969 | Shute | 128/344 |
| 3,626,949 | 12/1971 | Shute | 128/344 |
| 3,799,170 | 3/1974 | Walsh et al. | 128/344 |
| 3,848,602 | 11/1974 | Gutnick | 128/344 |
| 3,882,852 | 5/1975 | Sinnreich | 128/344 X |
| 3,900,033 | 8/1975 | Leininger et al. | 128/344 |

Primary Examiner—John D. Yasko
Attorney, Agent, or Firm—Benjamin F. Lambert

[57] ABSTRACT

A novel inflatable device is disclosed for use in dilating various body cavities, and especially the human cervix, comprising an envelope member having an enlarged bulbous portion on one end, and a shield at the opposite end. The envelope member is inflatable with suitable gasses such as carbon dioxide, or liquids such as saline, distilled water and the like.

14 Claims, 6 Drawing Figures

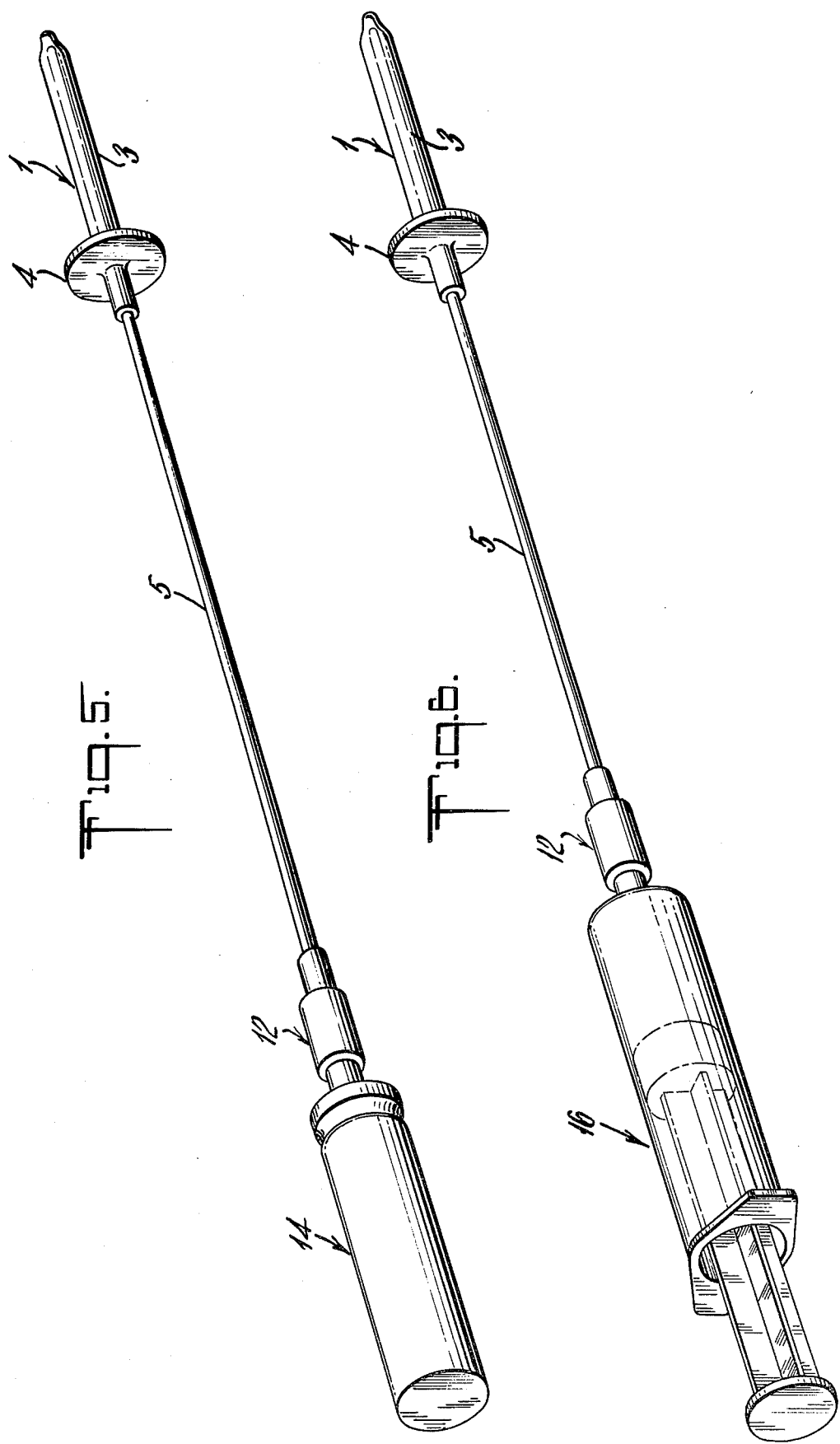

DILATOR FOR CERVICAL CANAL

This is a continuation-in-part of pending application U.S. Ser. No. 338,697, filed Mar. 7, 1973 and now U.S. Pat. No. 3,900,033.

In medical practice, dilatation of various canals is often necessary prior to performing specific surgical techniques, to relieve or remove a blockage, or to provide a clear passageway for surgical instruments or devices. For example, in performing a curettage of the uterus, it is usually necessary to dilate the cervix so that the curette may be inserted with a minimum of patient discomfort. Many more dilatation procedures of other body vessels would be performed depending upon the particular medical indication, if a relatively safe, physiologically safe and convenient dilatation procedure were available. That current dilatation procedures are insufficient to meet the needs of the physician and patient is illustrated by the problems encountered in cervical dilatation.

The human cervix is a canal having an inner and outer restricted os and varying in length from individual to individual, but usually of the order of about 2 centimeters. In terms of expandability, the canal itself is more elastic than either the inner or the outer os and as between the two, the inner os is much more restricted and intractable to dilatation than the outer os.

There are predominantly two major dilatation techniques that are employed in dilating the cervix. In one of these, an expansible dry solid material such as laminaria is inserted into the cervix in its dried, stiff form therein to come into contact with body fluids. The contact with the body fluids causes the laminaria to swell and thereby exert a transverse pressure on the canal, causing the canal to dilate. This procedure is extremely slow and typically involves often as much as ten to twelve hours for a significant amount of dilatation to occur. It is therefore wholly unsuited to current needs in the medical field.

A more widespread procedure involves the use of a series of solid, rodlike instruments of graduated diameter used in a serial fashion by the physician, e.g. Hegar dilators. The physician first inserts a rodlike dilator of low cross sectional area, removes the dilator and replaces it with the dilator of next higher cross sectional area. He continues this until adequate dilatation occurs. This normally takes two or three minutes and is usually accompanied by a distressing amount of pain and discomfort for the patient. Anesthetics are generally required but are not altogether satisfactory. For example, a general anesthetic has the disadvantage of requiring the presence of an anesthesiologist, thus complicating the procedure. When local anesthetics are used, the patient nevertheless frequently experiences a great amount of discomfort from the procedure. This is probably caused by the disproportionate amount of large longitudinal force required to achieve the relatively small amount of transverse force necessary to produce adequate dilatation. Administration of the local is itself not without discomfort.

The disadvantages of the current methods have been well recognized and have spawned a fair amount of activity in the field. Nevertheless, an effective, reliable, easily employed device and technique have not heretofore been available for use.

In the Polish Journal, Ginekologia Polska, Vol. 32, Number 8 (1961), pages 245-150, Stanislaw Sobieranski, Miroslaw Lewy and Zbigniew Piechowiak point out the severe risks attending current dilatation techniques. Uterine perforation, cervical laceration, and possible abdominal complications are consequences that can arise. This, of course, is in addition to the pain and discomfort that accompanies the procedure. The authors attempted to solve the problem by providing a rubber tube closed at one end and carrying a nylon net around the outer expanse of tubing. The device was inserted into the cervical canal and then filled with air to thereby exert a pressure on the cervix and cause dilatation. Two people were required to administer this technique, one being the person who inserted the device and the other being the person who manipulated the air pressure. Undoubtedly, two manipulators were required because the application of pressure caused the rubber tube to be expelled from the cervical canal either inwardly into the uterus, if it had been inserted too deeply, or outwardly into the vaginal canal if not inserted deeply enough. Thus, one person was needed to hold the tube in position to make certain it would be maintained in the canal, while the other was needed to attend to the flow of air. This technique is disadvantageous for obvious reasons.

In accordance with the present invention, a dilatation device is provided which relatively painlessly and effortlessly produces dilatation of a body canal, especially the cervical canal, when employed by one practitioner only. A full and complete understanding of the invention will be aided by reference to the accompanying drawings wherein FIG. 1 shows a specific embodiment of the device of the invention.

FIGS. 5 and 6 show the device with pressurizing means.

Figure 1:
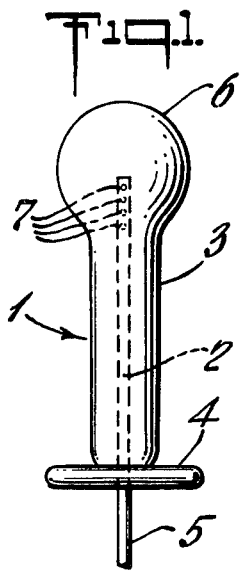

In FIG. 1 there is depicted at 1 a typical dilator of the present invention in inflated form but outside the body canal. In general, the device comprises an inserter tube 2 shrouded by a collapsible, relatively non-expansible envelope 3 having (in its non-collapsed form) a relatively constant cross sectional diameter. Envelope 3 is attached at one of its ends to shield 4 and is engaged in fluid tight relationship with the insertion tube 2 and shield 4. Projecting through shield 4 and coordinating with tube 2 is extension tube 5. The device is inserted in a manner described in more detail herein below, such that the shield 4 is the proximal end and enlarged portion 6 represents the distal end. Tube 2 is provided with preferably a plurality of ports 7 so that gas or liquid may be transmitted through the tube into the envelope 3. Tube 5 is connected to a source of fluid pressure, as shown in FIGS. 5 and 6. The fluid is preferably a chemically inert, physiologically acceptable fluid such as carbon dioxide, saline solution, distilled or sterile water and the like.

Figure 2:
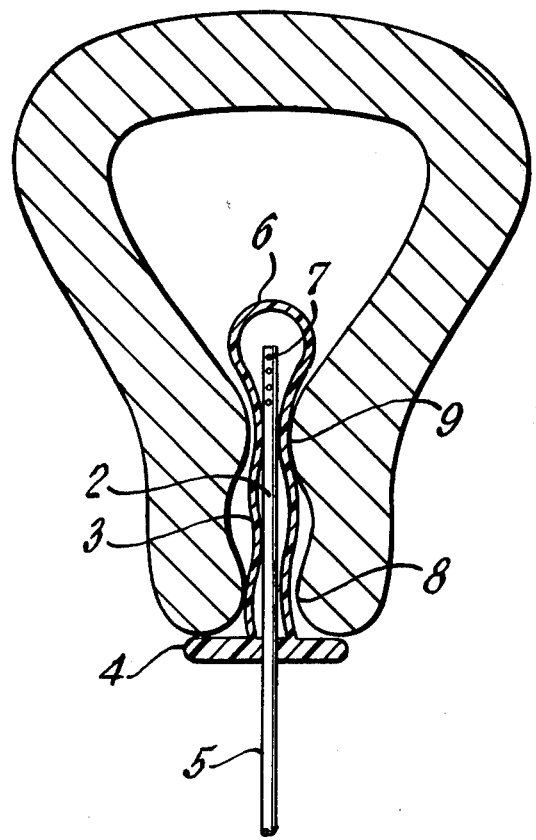
FIGS. 2 and 3 show the position of the device in place in a cervix.

The use of the device in the present invention will now be described in connection with the dilatation of the human cervical canal, but it is to be understood that the procedure and the device may be modified to accommodate any dilatable body canal or vessel. In accordance with the preferred embodiment in the present invention, device 1 is inserted into the human cervix without prior dilatation. The distance between the shield 4 and enlarged portion 6 is sufficient to permit contact along the entire length of the cervix by tube 3 including the inner os 9 and outer os 8. FIG. 2 shows the presence of the device of the invention in collapsed form, in place in the cervix to demonstrate that enlarged portion 6 is located beyond the inner os 9. Envelope 3 is preferably 2-3 centimeters long. While the human cervical canal is approximately 2 to 2.5 cm. long, it is desirable to have envelope 3 somewhat longer to ensure adequate occlusion. For devices used to dilate other canals, appropriate changes in dimension may be made as desired.

In order to facilitate insertion of the device, it is preferred that the diameter of tube 3 in its collapsed state be of the order of 2-4 millimeters. Tube 2, preferably provided as a rigid or semirigid member such as plastic, stainless steel and the like, being shrouded with a small diameter envelope, may then be easily inserted. Preferably the end of tube 2 comes into close proximity with the end of enlarged portion 6 although in FIGS. 1 and 2 it is shows at a significant distance therefrom.

Envelope 3 is made of a relatively non-elastic non-expansible material such as a polyurethane, polyvinylchloride or polyethylene vinyl acetate copolymer. Especially preferred are thermoplastic polyurethanes having a molecular weight of 20,000 to 80,000 and preferably 40,000 to 50,000 such as those available under the trade name of Roylar E-9 from the Uniroyal Corporation. Relative non-elasticity in the device in the present invention, it has been discovered, is important for two reasons. Since both the inner and outer ora are more intractable toward dilatation than the main part of the cervical canal, any member which is relatively elastic will tend to dilate the inner portion preferentially. Thus, if there were no restraints on the envelope 3, dilatation of the cervical canal would occur but corresponding dilatation of either os would not occur to the same degree. Ultimate insertion of a curette or other device would be impeded. Relative non-elasticity therefore ensures that both the inner and outer ora will be dilated to a degree closely approximating that of the canal itself (see FIG. 3). As used herein, the term "relatively non-elastic" is intended to have the same meaning as relatively inextensible and flexible. It has been discovered that when polyurethanes of the type mentioned above, having a collapsed diameter of 2-4 millimeters, and a filled diameter in the range of 12 to 20 millimeters, are used in the manner more completely described below, dilatation from about 8 to 12 millimeters will occur in about 2 to 10 minutes.

Once the device 1 is inserted into the cervix, fluid is permitted to flow into tube 5 through tube 2 out from ports 7 into envelope 3. Since the device is equipped with an enlarged portion, and since enlarged portion 6 is not restrained by engagement with any body tissue, introduction of fluid pressure into the system causes enlarged portion 6 to inflate first. Envelope 3, meeting resistance from the walls of the cervical canal, starts to fill up at a rate slower than that of enlarged portion 6. Thus, the differential response of the enlarged portion 6 vis-a-vis envelope 3 prevents device 1 from being expelled in an outward direction. As fluid flow continues, shield 4 prevents an inward slide of the device. The device is then charged with about 4-9 and preferably 5-8 pounds per square inch of gauge pressure with any convenient source of physiologically acceptable fluid. Gaseous carbon dioxide is preferred although liquids, such as saline, are also quite suitable.

As indicated above, the envelope of the dilator can be inflated by employing a gaseous or liquid fluid. It is preferred to utilize a one-way positioned at the junction 12 of the device and the reservoir containing the fluid. The valve can be prepared from any suitable material but valves prepared from plastic materials have been found to be most suitable. Where gaseous fluids are employed, the gas can be charged into a suitable cannister 14 such as that depicted in FIG. 5. Where a liquid fluid is employed, the fluid is stored in a container such as a syringe 16, for example (FIG. 6). In a preferred embodiment of the invention, after the container is filled to the desired volume, it is bonded to the one-way valve with a suitable adhesive. Suitable self-curing, solvent based or hot melt adhesives, such as a self-curing cyano acrylate, for example, may be employed. When bonded in this manner, a unitized dilator such as that depicted in FIGS. 5 and 6 is obtained. Where the unitized device is employed, the danger of overinflating the envelope is removed since a predetermined amount of fluid is employed. Thus the body canal is dilated only to the extent necessary to carry out the intended operation. In this way, the risk of causing injury to the person through over-inflation of the dilator is minimized.

In one embodiment of the invention, an aerosol-type container is employed to contain the gaseous fluid. The cannister can be made of any suitable material, such as aluminum, glass or plastic. The valve of the cannister can be a toggle (side activated), a vertical (upright) or a metering valve. The preferred combination is an aluminum cannister with a toggle valve. The valve is attached to the cannister by techniques known in the art and the cannister is charged with the gaseous fluid. The pressure inside the cannister may range from about 15 to 25 psig; the preferred range, however, is about 20-22 psig. The valve is adapted so that the cannister stem fits snugly into the open end of the dilator and depresses the diaphragm within. The envelope of the dilator can be evacuated prior to bonding by externally depressing the diaphragm of the valve.

When the dilator is positioned in the body opening, the envelope is inflated by simply pressing down the valve seat or by raising up the cartridge. This activates the release valve of the cannister and the contained fluid fills the entire system to an equilibrium pressure. When this occurs the back pressure from the dilator presses the diaphragm of the one-way valve against the cannister stem thus providing a positive seal which assures the continued inflation of the envelope. For example, with an initial cannister pressure of 20-22 psig, after inflation the envelope diameter would be 14-16 mm. and the equilibrium cannister pressure would be 10-12 psig. After the appropriate residence time, preferably 5-10 minutes, the envelope can be extracted from the body canal in the inflated state or it can be deflated by cutting the insertion/delivery stem. The entire unit can be discarded after use.

In another embodiment of the invention, a suitable, disposable, plastic syringe 16, preferably about 20 cc. in volume, is bonded to a one-way valve. The syringe barrel is completely filled with the liquid fluid and the excess is removed by means of the plunger through the valve until about 10-15 cc. of the fluid remains in the syringe. Care must be taken during this step to avoid entrapment of air in the syringe. The one-way valve/syringe bonded system can be force-fitted into the valve seat on the dilator in order to obtain a unitized system.

The envelope can be evacuated simultaneously by squeezing it.

When the dilator is positioned in the body canal, the envelope can be inflated by simply pushing the plunger of the syringe. The mechanism of activation is such that the pressure exerted by compressing the fluid opens the diaphragm of the one-way valve causing the envelope to fill up with the fluid. The back pressure of the fluid causes the diaphragm to be sealed and the envelope remains expanded without the maintenance of external pressure. For example, with a charge of about 10 cc. in the syringe, the expected diameter of the envelope would be about 14–16 mm. The expanded envelope can simply be pulled out of the body canal after the appropriate residence time or the envelope can be collapsed by cutting the insertion/delivery stem. The entire unit can be discarded after use.

Figure 3:
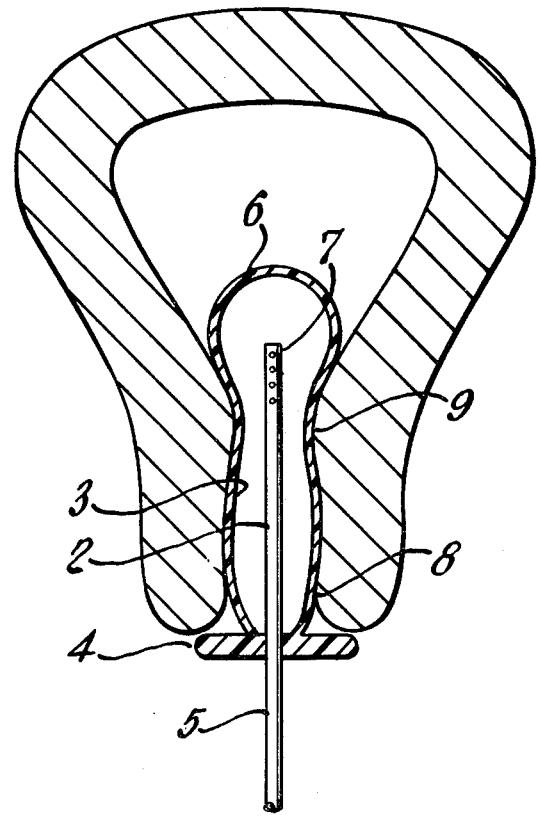

In consequence of the unique structure of the device in the present invention, only one person is needed to insert and charge the system. Once the system is charged, dilatation occurs within a very short period of time of the order of 2–3 minutes in a relatively painless fashion and without a general anesthetic. Thus, the patient may remain fully awake and aware at all times. In fact, it has been discovered that even a local anesthetic need generally not be used. Some practitioners may prefer to use a local anesthetic to ease the discomfort caused by the grip of the tenaculum on the cervix, but this would be encountered irrespective of the particular dilatation technique employed. FIG. 3 shows the placement of the device in the cervix following inflation. Both inner os 9 and outer os 8 are dilated to approximately the same degree. Following administration in the manner described, and when the patient is sufficiently dilated, the device may be removed and the patient treated in accordance with her medical indications. Oftentimes, the degree of dilatation is so satisfactory that the device may be freely moved in and removed from the cervical canal without venting the system.

With regard to dimensions of the various members of the dilator, it will be appreciated that these in a large measure depend upon the particular body canal being treated. For cervical use, shield 4 should be from 1–2 centimeters, and preferably 1.5 centimeters; tube 3 from 8–20 millimeters and preferably 10–12 millimeters in diameter in filled form and from 1.5–4 millimeters and preferably 2–3 millimeters in collapsed form; and tube 2 and tube 5 of the order of 1–1.5 millimeters in diameter. Obviously, for tracheal or esophageal use these dimensions should be increased and a sufficient amount of flexibility will be provided within each member so as to minimize the risks of perforation. It is apparent that modifications of the device may be incorporated which differ from those set forth in the description of the preferred embodiment, but it is believed that these are well within the skill of the art. Thus, for example, port 7 need not necessarily be located on the side but may be present as the open end of tube 2. Similarly, the seal between shield 4 and envelope 3 may be either at a point located on the shield itself away from the entry point of tube 2, or indeed, may be located at a point on tube 2 away from shield 4. Similar modifications may be employed.

The device of the present invention is also uniquely suited to being used as a drug delivery system and thus dilatation and therapy can be accomplished simultaneously. Additionally, under some circumstances, it may not be necessary to dilate to any significant degree at all. An illustration of the former case is represented by a device 1 wherein enlarged portion 6 is impregnated with a suitable medicament. Dilatation of the cervix would then be accompanied by a slow leaching of the medicament from the device itself. This could be an important adjunct to the use of abortifacients and labor inducers. Additionally, envelope 3 may itself be impregnated with a drug so that contact with the cervical canal results in high local concentrations of medicament.

Figure 4:
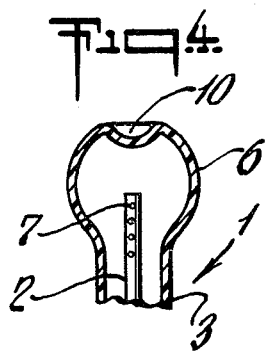
FIG. 4 shows a modification of the present device.

As an alternative to impregnation with a medicament, enlarged portion 6 may be fabricated with one or more depressions 10 as is shown in FIG. 4. This depression may be filled with medicament. When the device is inserted and fluid pressure applied, the pressure will force the depression 10 and cause the release of the medicament into the uterus.

In the following examples, unless otherwise indicated, a dilator of the type described in FIGS. 1 and 2 was employed. The envelope 3 has a filled unrestrained outside diameter of 12 millimeters, an envelope wall thickness of 0.25 millimeters, and enlarged portion 6 a maximum diameter of 15 millimeters. Tube 2 was stainless steel, although polyurethane tubes had been used in prior trials. Carbon dioxide was used as the inflation gas and in all patients except that of Example I, Lidocaine was used to minimize discomfort caused by the grasp of the tenaculum on the cervix.

EXAMPLE I

The patient was 16 years old, of zero parity and 6 weeks gestational age. No anesthesia was used because of a known allergic history. Pressurization at 4.5 psig for 3 minutes produced some cramping but less discomfort than use of the tenaculum and much less than produced by subsequent evacuation of the uterus by aspiration. After removal of the dilator, an 8 millimeter curette could be introduced with only slight resistance.

EXAMPLE II

The patient was 19 years old, of zero parity and 7 weeks gestational age. Pressurization at 5 psig for 2 minutes followed by 6 psig for another 2 minutes produced no discomfort. Final dilatation was somewhat more than 9 millimeters.

EXAMPLE III

The patient was 24 years old, of zero parity and 8 weeks gestational age. There was some discomfort at 5 psig pressure which diminished after the first 2 minutes. After a total of 3 minutes at 5 psig, pressure was increased to 6 psig for one more minute. The final size was 9 millimeters. The unusual amount of time required for dilatation here was caused by a very firm cervix.

EXAMPLE IV

The patient was 20 years old, of zero parity and 7 weeks gestational age. Pressurization was 6 psig for 1 minute followed by 7 psig for 2 additional minutes. There was no discomfort noted and the final size was 9 millimeters.

EXAMPLE V

The patient was 21 years old, of zero parity and 8 weeks gestational age. After 3 minutes at 6 psig, dilatation was 9 millimeters.

In each of the foregoing examples except Example I, the inflated dilator could be easily moved in the cervical canal even to complete withdrawal and reinsertion with no discomfort. While this was not possible in Example I, the presence of a very firm cervix in the patient necessitated venting in order to achieve a zero discomfort level for removal.

What is claimed is:

1. A body canal dilating device comprising a relatively non-elastic, non-expansible, collapsible, inflatable envelope, having two portions, the first said portion in the inflated state having a relatively constant diameter and a length sufficient to occlude a canal having more than one os, and the other of said portions contiguous with the first said portion and being a terminal enlarged bulbous portion having a diameter in excess of said constant diameter in the inflated state, a tubular inserter member entering the first said portion and while inside thereof extending therethrough and into the inside of the other of said portions, a shield located in proximity of the entrance to the first said portion and engaged with said tubular member, said tubular member being adapted to permit entry into said envelope of a pressurizing fluid, and fluid pressurizing means integral with said tubular member at a point external to said envelope.

2. The device of claim 1 wherein said fluid pressurizing means has a predetermined amount of fluid therein.

3. The device of claim 1 wherein said fluid pressurizing means is a syringe.

4. The device of claim 1 wherein said fluid pressurizing means is a pressurized cannister.

5. The device of claim 4 wherein the fluid in said pressurizing means is carbon dioxide.

6. The device of claim 1 wherein said first portion is of a length sufficient to occlude the entire length of the human cervical canal.

7. The device of claim 6 wherein said first portion has a diameter in the inflated state of from 12 to 20 mm.

8. The device of claim 7 wherein said first portion in the collapsed state measures between 1 1/2 to 4 mm. in diameter.

9. The device of claim 8 wherein the first portion and said terminal enlarged bulbous portion are polyurethane having a molecular weight of between 20,000 and 80,000.

10. The device of claim 9 wherein said tubular inserter member is at least semirigid.

11. The method for dilating a body canal which comprises inserting the device of claim 1 into a body canal and actuating said fluid pressurizing means to introduce fluid into the envelope thereby causing dilatation of said body canal.

12. The method of claim 11 wherein the envelope is pressurized by means of a pressurized cannister having an equilibrium pressure of about 10 to 12 pounds per square inch.

13. The method of claim 11 wherein the envelope is pressurized by introduction of an aqueous fluid.

14. The method of claim 11 wherein the envelope is pressurized by the introduction of carbon dioxide.

* * * * *

UNITED STATES PATENT AND TRADEMARK OFFICE
CERTIFICATE OF CORRECTION

PATENT NO. : 4,137,922
DATED : FEBRUARY 6, 1979
INVENTOR(S) : ROBERT I. LEININGER; JOSEPH R. PRESTON; BRENTON R. LOWER

It is certified that error appears in the above-identified patent and that said Letters Patent are hereby corrected as shown below:

Column 1, line 68: "pages 245-150" should read -- pages 245-250 --.
Column 3, line 20: "shows" should read -- shown --.
Column 4, line 3: "one-way positioned" should read -- one-way valve positioned --.
Column 8, Claim 12: "The method of Claim 11 wherein the envelope is pressurized by means of a pressurized cannister having an equilibrium pressure of about 10 to 12 pounds per square inch." should read -- The method of Claim 11 which additionally comprises pressurizing the envelope by means of a pressurized cannister having an equilibrium pressure of about 10 to 12 pounds per square inch --.
Column 8, Claim 13: "The method of Claim 11 wherein the envelope is pressurized by introduction of an aqueous fluid." should read -- The method of Claim 11 which additionally comprises pressurizing the envelope by introduction of an aqueous fluid --.
Column 8, Claim 14: "The method of Claim 11 wherein the envelope is pressurized by the introduction of carbon dioxide." should read -- The method of Claim 11 which additionally comprises pressurizing the envelope by the introduction of carbon dioxide --.

Signed and Sealed this

Eleventh Day of December 1979

[SEAL]

Attest:

SIDNEY A. DIAMOND

*Attesting Officer*　　*Commissioner of Patents and Trademarks*